United States Patent
Quist et al.

(10) Patent No.: US 6,590,652 B2
(45) Date of Patent: Jul. 8, 2003

(54) FLOW THROUGH LIGHT SCATTERING DEVICE

(75) Inventors: Gregory Quist, Escondido, CA (US); Craig Tisserat, Alta Loma, CA (US)

(73) Assignee: PointSource Technologies, Inc., Escondido, CA (US)

(*) Notice: Subject to any disclaimer, the term of this patent is extended or adjusted under 35 U.S.C. 154(b) by 0 days.

(21) Appl. No.: 10/058,637

(22) Filed: Jan. 29, 2002

(65) Prior Publication Data

US 2003/0086087 A1 May 8, 2003

Related U.S. Application Data

(60) Provisional application No. 60/336,859, filed on Nov. 2, 2001.

(51) Int. Cl.[7] .................................................. G01N 21/00
(52) U.S. Cl. ........................................ 356/338; 356/343
(58) Field of Search ........................ 356/337, 338–343, 356/246, 244

(56) References Cited

U.S. PATENT DOCUMENTS

| | | |
|---|---|---|
| 3,770,351 A | 11/1973 | Wyatt |
| 3,901,602 A | 8/1975 | Gravatt, Jr. |
| 4,070,113 A | 1/1978 | Frazer et al. |
| 4,173,415 A | 11/1979 | Wyatt |
| 4,265,538 A | 5/1981 | Wertheimer |
| 4,548,500 A | 10/1985 | Wyatt et al. |
| 4,565,448 A | 1/1986 | Abbott et al. |
| 4,702,598 A * | 10/1987 | Bohmer ...................... 356/343 |
| 4,728,190 A | 3/1988 | Knollenberg |
| 4,906,094 A | 3/1990 | Ashida |
| 4,907,884 A * | 3/1990 | Philips et al. ................ 356/336 |
| 4,942,305 A | 7/1990 | Sommer |
| 4,952,055 A | 8/1990 | Wyatt |
| 5,125,737 A | 6/1992 | Rodriguez et al. |
| 5,247,340 A | 9/1993 | Ogino |
| 5,305,071 A * | 4/1994 | Wyatt .......................... 356/73 |
| 5,414,508 A | 5/1995 | Takahashi et al. |
| 5,436,465 A | 7/1995 | Borden et al. |
| 5,534,999 A | 7/1996 | Koshizuka et al. |
| 5,737,078 A | 4/1998 | Takarada et al. |
| 5,999,256 A | 12/1999 | Jones et al. |
| 6,023,324 A | 2/2000 | Myers |
| 6,100,541 A | 8/2000 | Nagle et al. |
| 6,118,531 A | 9/2000 | Hertel et al. |
| 6,120,734 A | 9/2000 | Lackie |

* cited by examiner

Primary Examiner—Michael P. Stafira
(74) Attorney, Agent, or Firm—Leon D. Rosen

(57) ABSTRACT

A system for identifying microorganisms and other microscopic particles in a fluid, includes a laser that directs a laser beam (14) through a detect zone (20) and a plurality of photodetectors (30) that detect light scattered in different directions from a particle at the detect zone, and includes a carrier (110) that confines fluid to movement along a narrow path. The carrier includes a glass sphere (112) with a passage (116) for carrying the fluid. The spherical surface allows light scattered at a large angle from the direction of the laser beam, to pass through the glass sphere to its outside for detection there.

6 Claims, 5 Drawing Sheets

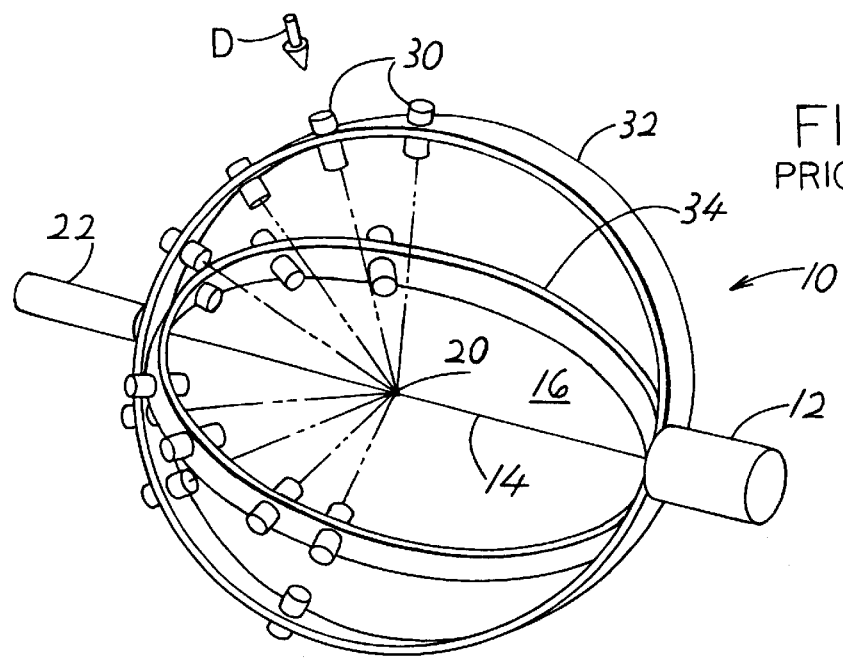
FIG. 1 PRIOR ART
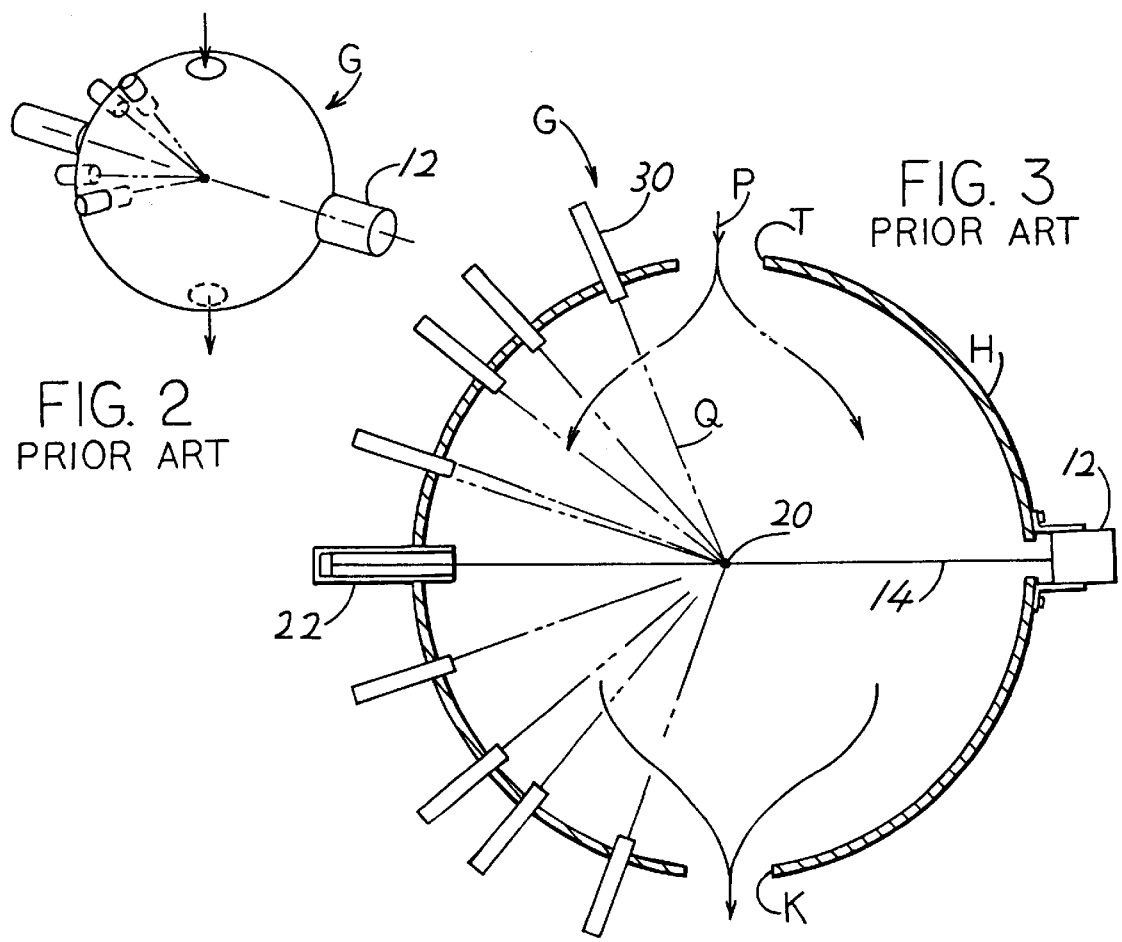
FIG. 2 PRIOR ART
FIG. 3 PRIOR ART

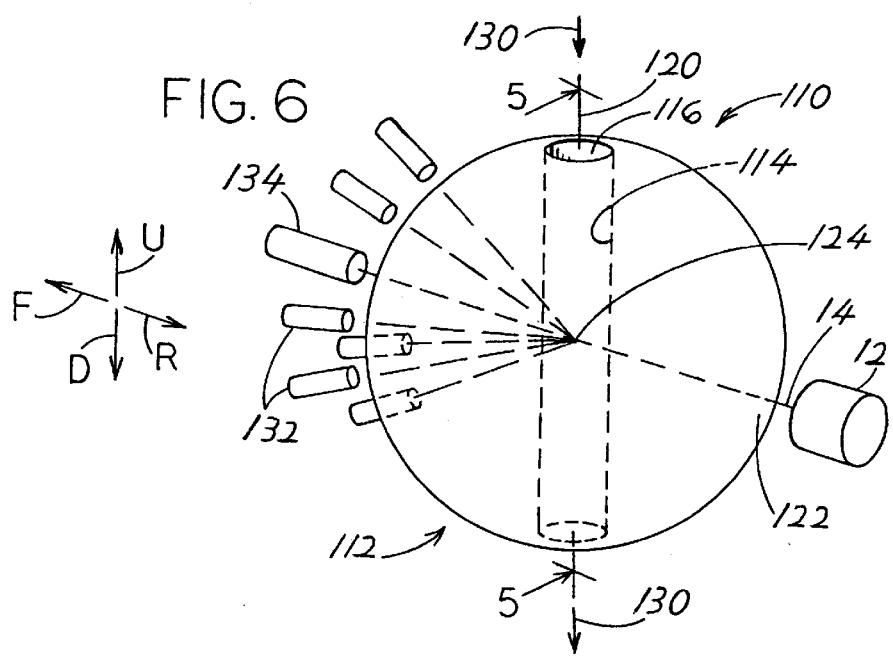
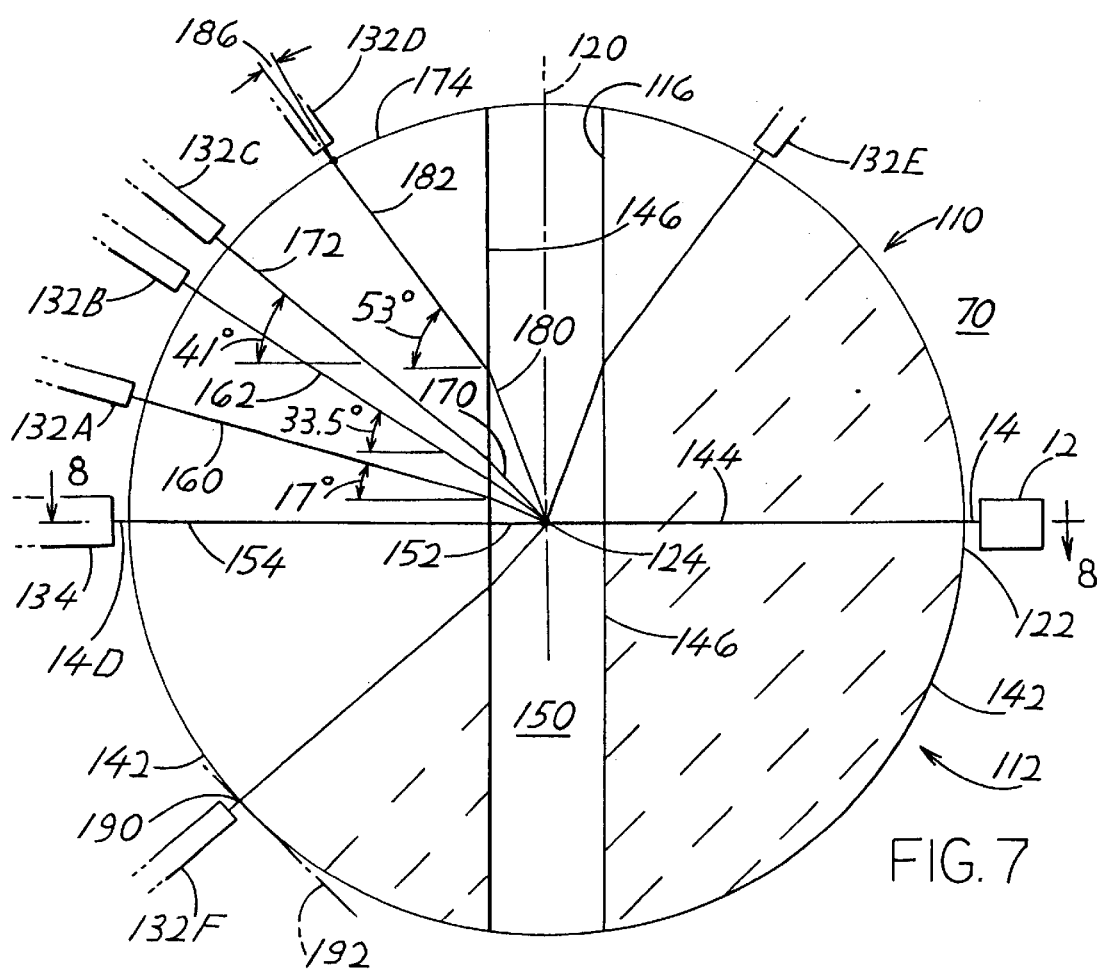

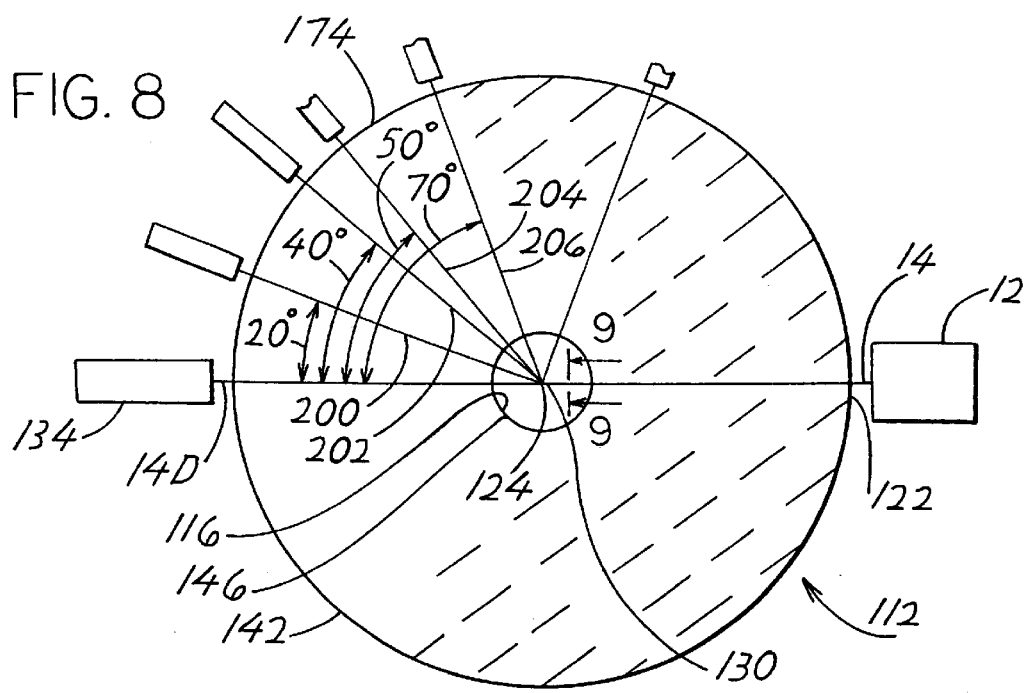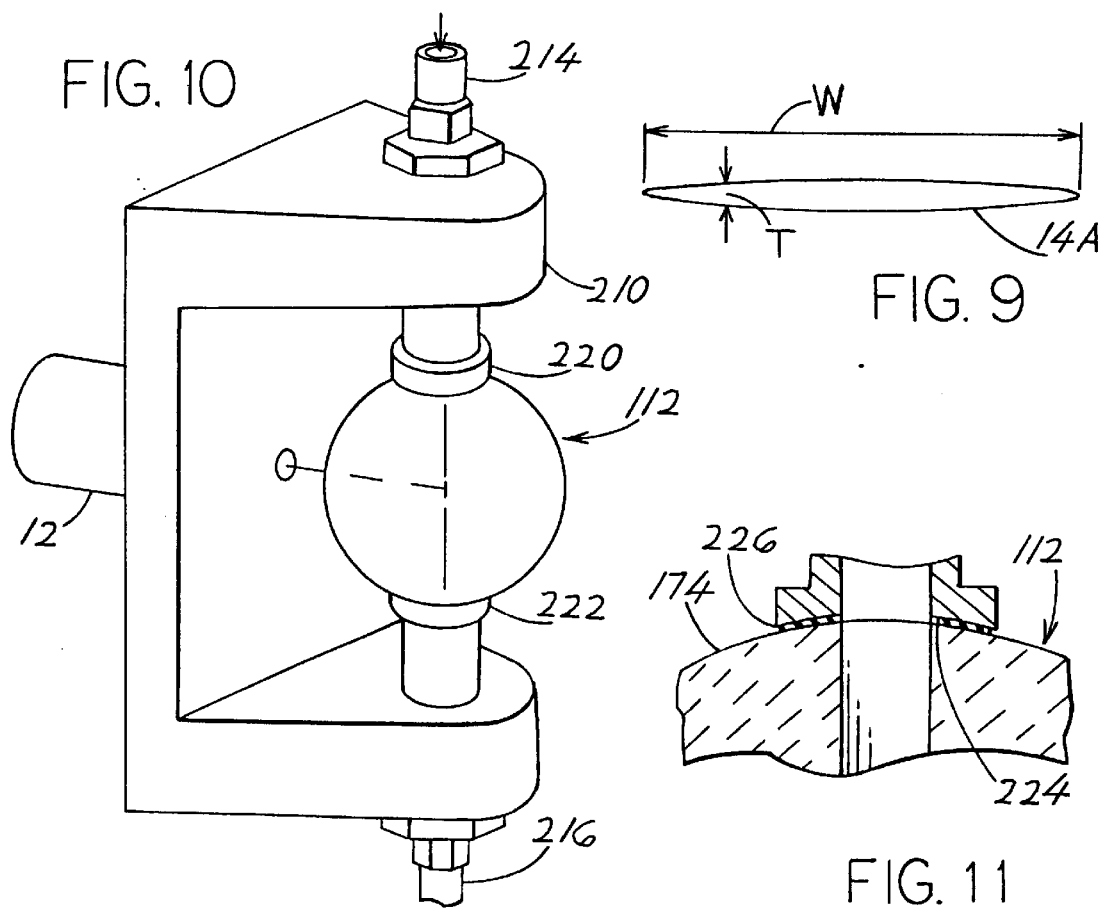

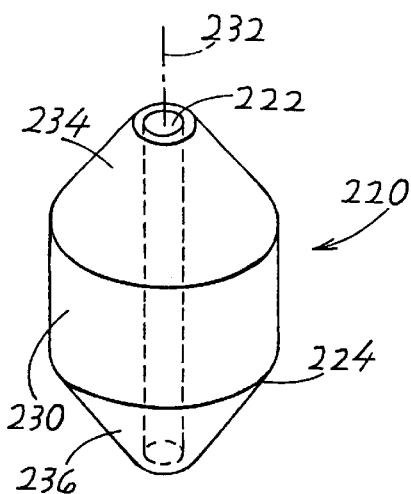
FIG. 12
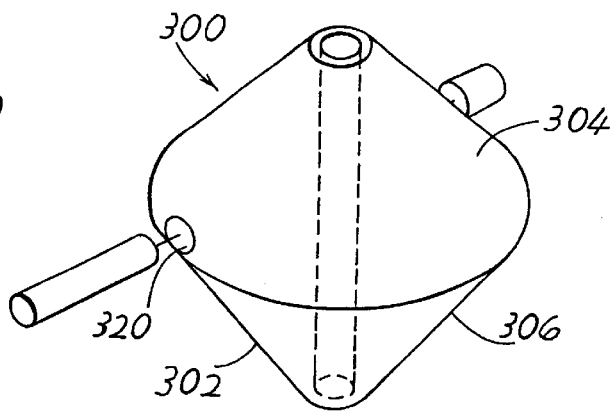
FIG. 14
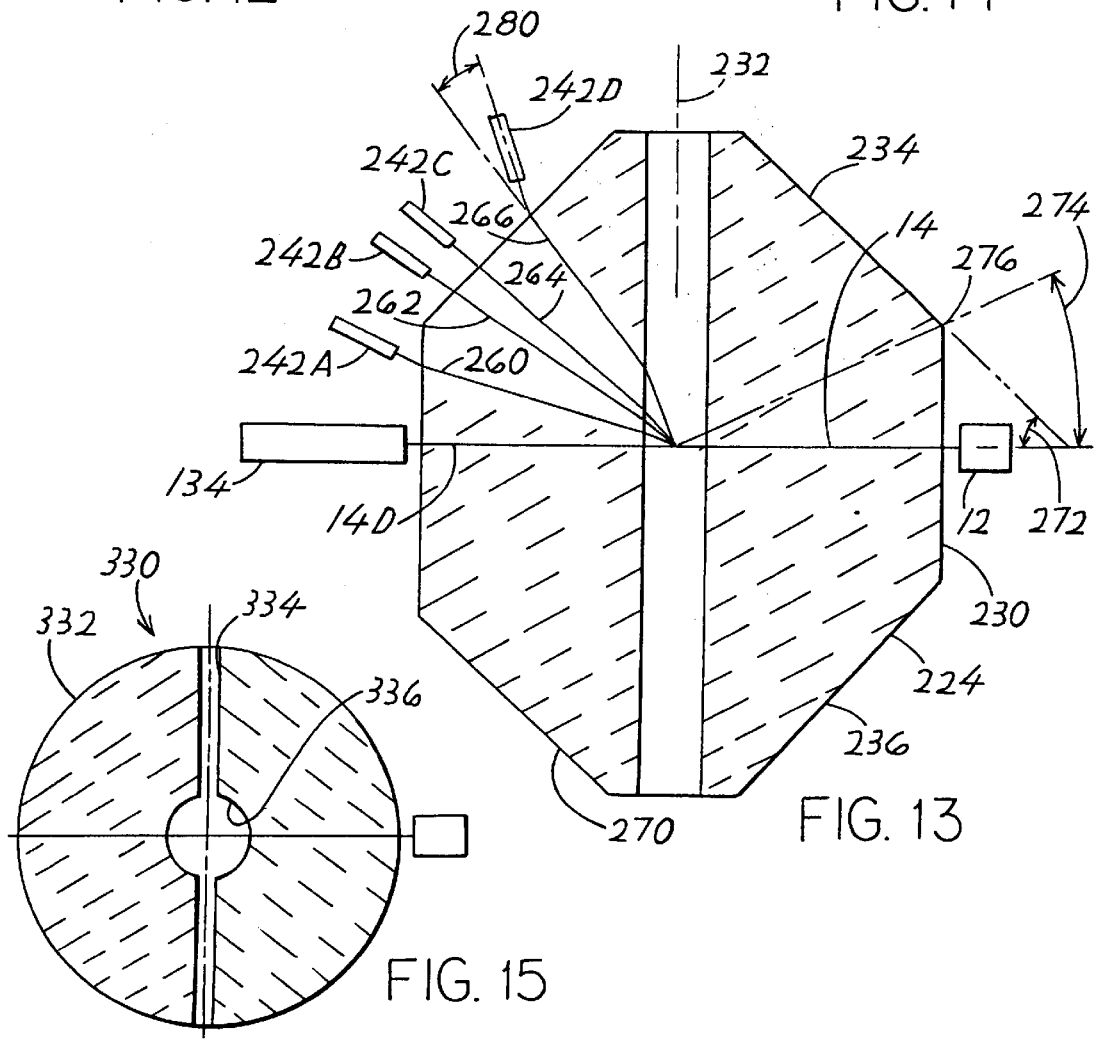
FIG. 13
FIG. 15

US 6,590,652 B2

FLOW THROUGH LIGHT SCATTERING DEVICE

CROSS-REFERENCE TO RELATED APPLICATION

Applicant claims priority from U.S. Provision application 60/336,859 filed Nov. 2, 2001.

BACKGROUND OF THE INVENTION

A microscopic particle such as a particular specie of bacteria lying in a fluid such as water or air, can be identified by detecting its pattern of light scatter when it passes through a light beam. A plurality of photodetectors detect light scattered in different directions from a laser beam. Although a laser beam and multiple photodetectors can be immersed in a contaminated fluid, this has a disadvantage that the laser and photodetectors may be coated with a slime or other material in the fluid and may become contaminated so that they require decontamination before they are handled. A system which enabled detection and/or identification of microscopic particles in a fluid by photodetectors that detect scattered light from a laser, which isolated the laser and photodetectors from the fluid, would be value.

SUMMARY OF THE INVENTION

In accordance with one embodiment of the present invention, an apparatus is provided for the detection and/or identification of microscopic particles in fluid, of the type that includes a light source and multiple photodetectors, which isolates the light source and photodetectors from the fluid and which confines fluid flow to a narrow path. The apparatus includes a solid light-passing material such as glass, having internal walls forming a passage through which flows fluid to be analyzed, and having an outside surface at or beyond which the photodetectors are positioned. The passage confines fluid flow to a narrow path that passes through the light beam, and the photodetectors are isolated from the fluid because they lie outside the glass carrier. In one system, the glass carrier is of spherical outside shape, and has a cylindrical bore extending from its top to its bottom. The spherical outer surface results in scattered light passing out of the sphere in a direction largely normal to the surface of the sphere.

The novel features of the invention are set forth with particularity in the appended claims. The invention will be best understood from the following description when read in conjunction with the accompanying drawings.

BRIEF DESCRIPTION OF THE DRAWINGS

FIG. 1 is an isometric view of a particle identification system that is largely of the prior art.

FIG. 2 is an isometric view of a prior art system.

FIG. 3 is a sectional side view of the prior art system of FIG. 2.

FIG. 6 is an isometric view of a system of another embodiment of the invention, wherein the carrier has a largely spherical outside shape.

FIG. 7 is a sectional view of the carrier of FIG. 6, showing the paths of light scattered from a particle in water, through the water, through the glass of the carrier, and into the surrounding air.

FIG. 8 is a sectional view taken on line 8—8 of FIG. 7.

FIG. 9 is a sectional view taken on line 9—9 of FIG. 8, showing the cross sectional shape of the laser beam.

FIG. 10 is an isometric view of a fluid handling system that includes the spherical carrier of FIG. 6 and apparatus for sealing to it and for flowing fluid through it.

FIG. 11 is a sectional view of a portion of the system of FIG. 10, showing the transition between an input conduit and the glass sphere.

FIG. 12 is an isometric view of a carrier constructed in accordance with another embodiment of the invention, wherein the outer surface of the carrier is divided into three bands that are differently angled from the axis of the carrier.

FIG. 13 is a sectional view of the carrier of FIG. 12.

FIG. 14 is an isometric view of a carrier of another embodiment of the invention, wherein the outside of the carrier has only two bands that are differently angled from the axis, and flat spots for a light beam to enter and leave the carrier.

FIG. 15 is a sectional view of a carrier suitable for identifying particles in air.

DESCRIPTION OF THE PREFERRED EMBODIMENTS

Figure 4:
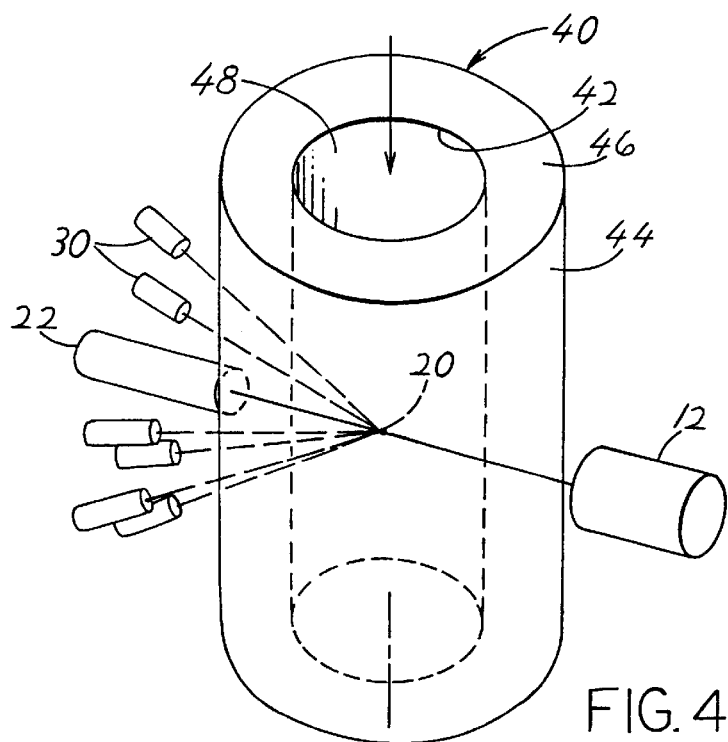
FIG. 4 is an isometric view of a system of one embodiment of the invention.

FIG. 1 shows a scatter detect system 10 which includes a laser 12 that generates a narrow laser beam 14 that passes through fluid 16. One example is a laser beam of red light of a wavelength of 0.6 microns, and a fluid 16 which is water that may contain pathogenic bacteria. The light can extend from infrared through visible to ultraviolet and to far ultraviolet or even soft x-rays. The laser beam passes through a detect zone 20 to a dump 22 that captures most of the laser beam energy. The fluid moves along the direction of arrow D to carry the particles to be identified, some of which will pass through the detect zone 20 lying along the laser beam. When a particle passes through the detect zone, light of the laser beam is scattered by the particles. The scattered light (including light generated by luminescence) is detected by several detectors such as photodetectors 30. The outputs of the several detectors can be analyzed by a computer program designed to identify the particle. We note that it is useful to merely detect the presence and/or number of particles per unit volume in some applications (e.g. to test purified water to be used in scientific analysis).

The detectors 30 can be diodes that change resistance, diodes that generate current, charge coupled diodes, locations on a film, etc. The photodetectors 30 in FIG. 1 lie on two circular rings 32, 34 the lie in perpendicular planes. Each photodetector detects only light received within a narrow angle such as 2°, to detect only light originating from the detect zone. Information about the scatter pattern helps to analyze the particles that pass through the detect zone 20.

It is useful to detect the scattering pattern of a variety of particles, including organic and nonorganic materials, bacteria, cells, ice crystals, dust, and minerals. Scattering patterns of particles can be used to classify the particles or to characterize the particles in size, shape, orientation, composition, geometry, and other physical properties. One use for the scatter detector system is to identify a species of pathogenic microorganisms found in a water supply.

The system 10 of FIG. 1 can be used to detect particles in water by immersing the system in water. This has many disadvantages, including the fact that the water may corrode parts of the system such as the photodetectors 30 and may coat them with biological films that can form on immersed surfaces. It is often desirable to test a moderately small sample of fluid, so it would be desirable if the fluid passed through a container or carrier of smaller diameter than the entire system 10. Some fluids may contain pathogens, and it is desirable to not contaminate the different components of the system 10 with such pathogens.

FIGS. 2 and 3 illustrate a prior art system G which includes a shell H, a laser 12 and dump 22 aligned with openings in the shell, and a plurality of photodetectors 30 that detect scattering of the laser beam 14 from a detect zone 20 lying along the laser beam. Fluid such as water with particles is passed into the shell through an opening J and exits the shell through another opening K. The fluid paths P bring the fluid to all parts of the shell, including the detect zone 20.

The system G has the advantage that light scattered from the detect zone 20 can reach a photodetector 30 while moving only along a medium of constant index of refraction. The index of refraction for air is 1.0 while the index for water is about 1.33. As a result, each path of scattered light, such as path Q, is a straight line from the detect zone 20 to a photodetector 30. However, the system G has disadvantages, including the fact that the photodetectors 30 are exposed to the fluid in the shell, and may be coated with a biological film, or slime, and may be contaminated with pathogens in the fluid. It can be appreciated that cleaning portions of the photodetectors 30 that project into the shell can be very difficult without removing the photodetectors. Only a very small percent of fluid flowing through the shell passes through the detect zone 20, since the cross section of the spherical shell in a horizontal plane that includes the laser beam 14, is very large. Accordingly, a large amount of fluid is required to obtain a given number of particle detections. In addition, if water is the fluid that carries the particles, then a rapid flow of water through the shell could result in cavitation where the photodetectors 30 and dump 22 project into the shell, resulting in tiny bubbles that can deflect scattered light.

FIG. 4 illustrates a carrier 40 formed by a glass pipe having cylindrical inside and outside surfaces 42, 44. The laser 12 lies outside the glass pipe and directs a laser beam through one side of the glass wall 46 of the pipe and through the axis 50 of the pipe. The laser beam passes through fluid such as water lying in the pipe and exits through an opposite side of the wall 46 of the pipe. When a particle passes through the detect zone 20 that lies on the axis of the pipe, light is scattered by the particle, passes through the walls 46 of the pipe, and is detected by photodetectors 30 lying outside the pipe. The cylindrical glass carrier 40 provides the advantages that the laser 12, dump 22 and photodetectors 30 are all isolated from fluid in the passage 48 that extends through the glass pipe. Also, the passage 48 can be made to have a moderately small diameter so that a greater proportion of the particles in the fluid will pass through the detect zone, to allow an analysis using a smaller sample of fluid. However, the carrier 40 has certain disadvantages, including the fact that light scattered at a large angle to the horizontal will not pass through the glass wall 46 of the pipe, as explained below.

Figure 5:
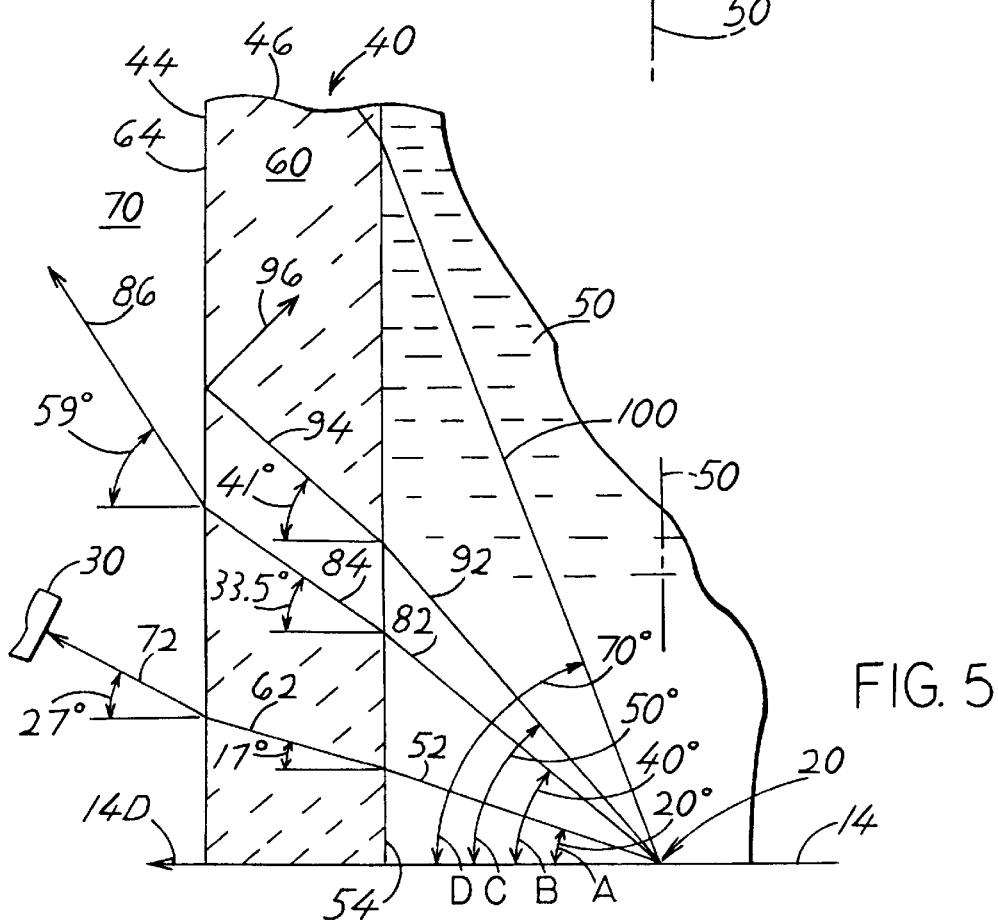
FIG. 5 is a sectional side view of a portion of the system of FIG. 4, showing the paths of scattered light through water, through glass of the carrier, and into air surrounding the carrier.

FIG. 5 shows that paths of light scattered by a particle in the detect zone 20 that lies along the laser beam 14. The laser beam travels along the laser beam direction 14D which is perpendicular to the passage axis 50. The detect zone 20 that particles pass through, lies in water 51 that is contained in the fluid container or carrier 40 whose wall 46 has inside and outside cylindrical surfaces. Light scattered by a particle in the detect zone 20 and that moves along the path portion 52 that is inclined by an angle of 20° from the laser direction, passes through the interface 54 between the water 51 and the glass 60 of the carrier walls. The index of refraction of water is 1.33, while the index of refraction of one common type of glass is 1.55. As a result, the scattered light moves through the glass along a path portion 62 that is angled 17° from the horizontal laser direction. When the scattered light emerges from the interface 64 between the glass and air 70, the light moves along a path portion 72 that is angled by 27° from the laser direction 14D.

Light moving along path portion 72 is detected by one of the detectors 30.

Similarly, light scattered from the detect zone 20 and moving at an angle B of 40° from the laser beam direction 14D moves along a path portion 82. The path portion 84 in the glass is angled 33.5° from the laser direction 14D. The light continues in the air along path portion 86 that is angled 59° from the laser direction, to another detector.

Light scattered from a particle at the detect zone 20 at an angle C of 50° from the laser beam direction 14D will move along path portion 92. The light then moves in the glass along path portion 94 which is at an angle of 41° from the laser beam direction 14D. However, when the beam moving along path portion 94 encounters the interface 64 between the glass and air, the beam will be reflected from the container outer surface 44 along path portion 96.

When light passes from a medium of high index of refraction such as glass having an index of 1.55, to a medium of lower index of refraction such as air with an index of 1.0, there is a critical angle beyond which all light is reflected from the interface rather than passing through it. For glass having an index 1.55, the critical angle is 41° at a glass-air interface. For a glass having an index of 1.50, the critical angle is 42°. As a result, in FIG. 5, only light scattered at an C angle less than plus or minus 50° from the horizontal laser beam direction 14D will pass out of the fluid carrier. Important information can be obtained by scattering of light at angles greater than 50°, and it is desirable that the transparent container allow the detection of light scattered at more than 50° from the beam direction.

FIGS. 6–8 illustrate a container or carrier 110 of the present invention, which enables the laser and photodetectors to lie isolated from the fluid, while allowing the detection of lights scattering at a wide angle from the beam direction. FIG. 6 shows that the carrier is in the shape of a largely spherical lens 112 with glass walls 114 forming a passage 116 in which fluid can be contained or through which fluid can pass, where the fluid contains particles whose scattering patterns are to be detected. The bore that forms that passage 116 is of cylindrical shape with smooth walls, and has an axis 120. It would be possible to have a cylindrical shape only on the front side of the passage, which is furthest from the laser, if the photodetectors are located only forward of the passage. A complete (360° around the axis) cylindrical bore can be readily machined in a single piece of glass of the spherical lens.

The beam 14 generated by a laser 12, passes into one side 122 of the spherical lens and passes through the axis 120 that lies at the center of the cylindrical passage. A detect zone 124 lies at the intersection of the laser beam and the axis 120. The fluid flows along the downward direction of arrow 130 through the passage, and some particles in the fluid will pass through the detect zone. Whenever a particle passes through the detect zone, light from that particle will be scattered. FIG. 6 shows photodetectors 132 positioned to detect light scattered from the detect zone 124. The photodetectors are positioned to detect light that passes along predetermined paths to the locations of the photodetectors. Most of the laser beam energy reaches the dump 134 where it is absorbed. It would be possible to form blind bores in the outer surface into which the photodetectors are inserted, but there is generally no need to do so.

FIG. 7 shows that the laser beam 14 initially passes through air 70, and then passes through the air-glass interface 142 at the rear side 122 of the spherical lens. The laser beam moves along path 144 that carries it through the glass-fluid interface 146. Assuming that water 150 is the fluid in the passage 116, the interface 146 is a glass-water interface. The beam then passes through the detect zone 124 where light of the beam is scattered by any particle that lies in the detect zone. Most of the light continues along the path portion 152 in the water, along the path portion 154 in the glass, and through the air into the dump 134.

Light scattered at an angle of plus 20° and plus 40°, move along paths 160, 162 to photodetectors 132A, 132B. The laser beam path 14D is assumed to be horizontal. Light scattered at an angle of 50° from the horizontal, from the detect zone 124, passes along the path portions 170, 172 with path portion 172 being angled at 41° from the horizontal. When light moving along the path portion 172 encounters the glass-air interface 142, the light passes approximately normal to, which means perpendicular to or at an angle of 90° to, the surface 174 of the lens at the location of the beam 172. Accordingly, the light at path 172 does not change direction appreciably, but continues substantially along the direction of path 172 to the corresponding photodetector 132C. Similarly, light scattered from the detect zone 22 at an angle of more than 50° from the laser beam direction 14D would pass through the lens to a detector.

It is noted that light scattered at an angle approaching 80° to the laser beam direction, will be reflected at the interface 146 between the water and glass, and normally cannot be detected. However, the glass surface of the passage, at the interface 146, can be coated with a nonreflecting coating to increase the scatter angle that can be detected.

FIG. 7 shows light scattered from the detect zone 124 at an angle of 70° to the horizontal and moving along a path 180. The light then moves along a path portion 182 within the lens, which is angled 53° from the horizontal. There is a small angle 186 of about 8° between the spherical surface 174 along the beam, and the direction of the beam 182. However, since the angle is far less than the critical angle of 41°, the light will pass through the interface and be detected by a photodetector 132D. It is possible to use a slightly oval carrier to avoid this, but this is generally unnecessary. It is noted that photodetectors such as 132E can detect light scattered more than 90° from the direction of the laser beam. Also, detectors such as 132F are positioned to detect light scattered at a downward angle (and forward or rearward). It is noted that an outer surface portion 190 where light emerges that is detected by detector 132F, forms a tangent 192 that extends at a downward incline and toward the axis 120.

FIG. 8 is a sectional view taken downwardly along the axis 130 of the spherical lens 112. This view shows light moving along paths 200, 202, 204 and 206, which lie in a horizontal plane in which the laser beam direction 14D lies. The beams 200–206 are scattered at angles of 20°, 40°, 50° and 70° respectively from the laser beam direction. Since the detect zone 124 lies on the axis of the passage 116, all scattered light passes through the water-glass interface 146 in a direction normal to the interface, and its path does not deviate from the original scatter direction. Similarly, when the scattered light passes through the glass-air interface 142, the scattered light passes precisely normal to the lens outer surface 174 and does not deviate from its original path.

FIG. 9 shows the shape of the cross section of the laser beam at 14A, as it passes through the axis of the spherical lens. The laser beam has a small width W such as 1.5 mm and an even smaller average thickness T such as 0.1 mm at the detect zone. FIG. 8 shows that at the rear side 122 of the lens, where the laser beam initially enters the lens, the convex surface of the lens tends to converge the laser beam. If the radius of the spherical lens 112 is insignificant with respect to the width W of the laser beam, the effect will be insignificant. Where the effect is significant, applicant can provide optics between the laser 12 and the lens rear surface 122 and/or take into account the effect of the interfaces, while also taking into account the fact that the laser beam tends to expand in width and thickness at locations progressively further from the laser.

In an apparatus of the type illustrated in FIGS. 6–8 that applicant has constructed and tested, the spherical lens 112 was constructed of a high quantity glass that is substantially free of defects that could cause scattering that leads to erroneous detection. The sphere had an outside diameter of 6.4 cm and a passage 116 having a diameter of 9 mm. The passage 116 was formed by cutting a cylindrical hole and precisely polishing it to create a smooth passage for minimum light scattering and distortion. The sphere was mounted with the cylindrical hole extending vertically, so water can be flowed downwardly by gravity flow from a small receptacle. The container or carrier can be used to carry gas (e.g. air containing particles) instead of liquid, and can be used even to hold a fluid that does not pass from one end of the passage to the other.

The diameter of the cylindrical passage 116 is preferably at least 4 times, and more preferably about 6 times, the width W of the laser beam. This is due to the photodetectors such as 132D in FIG. 7 preferably detecting the entire detection zone, which may have a width and length each about 1.5 mm.

FIGS. 10 and 11 show a set-up where the spherical lens 112 is held on mount 210 that has conduits in the form of pipes 214, 216 with lens-adjacent ends 220, 222, the pipes and their ends being designed for laminar flow. As shown in FIG. 11, each pipe has a surface 224 that is machined to correspond precisely with the surface of the spherical lens outside surface 174. A thin elastomeric washer 226 lies between the pipe surface 224 and the outside surface 174 of the spherical lens to seal the connection. FIG. 10 shows that the spherical lens 112 is fixed in place by being clamped between the pipe ends 220, 222. The convex lens surfaces around the passage, and the concave pipe surfaces, prevent sideward movement of the lens. A laser, dump and detectors are held by a separate frame.

FIGS. 12 and 13 illustrate another carrier 220 with a cylindrical passage 222 and with an outside surface 224 that includes a cylindrical band 230 at the middle of the height (and centered on axis 232), and top and bottom conical bands 234, 236. As shown in FIG. 13, a laser 12 generates a light beam 14 that moves in a horizontal direction 14D to the dump 134. A plurality of photodetectors 242A, 242B, 242C and 242D detect light that is scattered along paths 260–266. The light moving along the paths 260–266 are initially scattered from the detect zone 124 at angles of 20°, 40°, 50° and 70°, respectively, from the horizontal laser beam direction 14D. The scattered light passes through the glass-air interface 270 at only a small angle to the surface.

In one example, the angle 272 of the conical band from the horizontal, as seen in the sectional view of FIG. 13 taken along the axis 232, is 45° and the angle 274 between the detect zone 124 and the lower end 276 of the upper conical band is 25°. In that case, the angle 280 between the scatter light path 266 representing a scatter angle of 70° from the horizontal, and a surface location of the band 234 is only about 10°.

FIG. 14 illustrates still another carrier 300 wherein the outside surface 302 includes only upper and lower conical bands 304, 306. This results in a large angle between the outer surface 302 and the path of light emerging from the glass into air at a small scatter angle such as below 10° or 20°, and is not preferred. Flat spots 320 are provided at opposite sides for entrance of the laser beam into the carrier and exit of the laser beam into the dump.

FIG. 15 shows another carrier 330 that is especially useful for passing air that contains particles. The carrier has a spherical outer surface 332. The passage 334 has a spherical chamber 336 to minimize deflection of scattered light.

Although applicant has illustrated carriers of light-transmitting material (usually transparent) with cylindrical passages, it is possible to use other shapes of passages. When the fluid that carries particles is a liquid, it is desirable that the cross section of the passage remain constant or deviate only several degrees from a constant direction, to avoid non-laminar flow and a consequent generation of microscopic bubbles that can deflect light. Applicant usually places the photodetectors forward of the detect zone (the laser beam is assumed to be moving forwardly) so it is possible to not use light-transmitting material rearward of the detect zone, or elsewhere where the photodetectors are not located.

Although applicant shows the fluid moving downwardly, it could be made to flow in any direction, so terms such as "downward", "horizontal", etc. refer to the apparatus as it is illustrated but the apparatus can be used in any orientation with respect to the Earth.

Thus, the invention provides a carrier through which fluid containing particles can flow to enable detection and identification of the particles, which keeps a light source such as a laser and photodetectors separate from the fluid, and which confines the fluid to a passage of relatively small cross section so that a substantial portion of the fluid passes through a detect zone of a laser beam. The apparatus includes a carrier formed of light-passing material such as glass, with an outer surface that leads to the photodetectors or photodetector locations. The carrier preferably has outer surface portions above and below a horizontal plane in which the light beam lies, that are each angled from the axis, including an upper surface portion that is inclined at an upward incline toward the passage axis and a lower surface portion that is inclined at a downward incline toward the axis. The carrier can be formed as substantially a sphere, so that all light emerging from the spherical surface extends largely normal to the spherical surface location from which it emerges. The passage can be formed as a cylinder around all or only part of the axis, or its front can be flat or of another shape. However, a cylindrical bore is the easiest to machine, and avoids the need to use two pieces of glass that must be held together. A piece of glass that forms the carrier, can be coupled to conduits with surfaces that are pressed against the top and bottom of the carrier so the carrier is clamped between the surfaces of the conduits. The system can be used to detect the presence of microscopic particles in a pure fluid even if the particles do not have to be identified.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. Apparatus for at least detecting particles in a fluid, which includes a light source that generates a light beam that moves along a beam path through a detect zone, and a plurality of detectors that detect light scattered in different predetermined directions by a particle lying at said detect zone, comprising:

a carrier formed of a solid transparent material, said carrier having walls forming a passage into which the fluid can pass and forming an outside surface, said detect zone lying in said passage and said detectors lying outside said carrier with said walls isolating said detectors from fluid in said passage;

said passage extends in a downward direction along an axis, said beam path extends in a forward direction, and said axis and beam path define a horizontal plane that is normal to said axis and that includes said beam path;

said outside surface of said carrier has a top surface portion that lies above said horizontal plane and that extends around said axis with said top surface portion extending at an upward incline toward said axis, and said carrier has a bottom surface portion that lies below said horizontal plane and that extends around said axis, with said bottom surface portion extending at a downward incline toward said axis.

2. The apparatus described in claim 1, wherein:

said outside surface of said carrier includes a middle band that is cylindrical and that is substantially centered on said horizontal plane.

3. Apparatus for at least detecting particles in a fluid, which includes a light source that generates a light beam that moves along a path through a detect zone, and a plurality of detectors spaced about said detect zone and oriented to detect light scattered in predetermined directions by a particle lying at said detect zone, comprising:

a carrier formed of a glass-like solid transparent material and having walls that form a through passage and an outer surface, at least a portion of said outer surface lying between said detect zone and said detectors being substantially spherical, so light scattered by a particle passing through said detect zone passes through said glass-like material and emerges largely normal to the outer surface before passing to one of said detectors;

input and output conduits for directing fluid into and out of said through passage;

said carrier having top and bottom surface areas surrounding upper and lower ends of said passage, respectively;

said input and output conduits having sealing surfaces that are of shapes corresponding to the shapes of said top and bottom surface areas and that are pressed facewise against said top and bottom surface areas to seal them against and to clamp said carrier in place.

4. The apparatus described in claim 3 wherein:

said top and bottom surface areas of said carrier are of convex spherical shapes and said sealing surfaces of said conduits are of concave spherical shapes.

5. Apparatus for at least detecting particles in a fluid, which includes a light source that generates a light beam that moves in a light beam direction along a path through a detect zone, and a plurality of detectors for detecting light scattered in predetermined directions by a particle lying at said detect zone, comprising:

a carrier formed of a glass-like solid transparent material and having walls that form a through passage and an outer surface, said glass-like material filling the volume between said passage and said outer surface, at least a portion of said outer surface that extends at least 41° from said light beam direction, as measured about a center point lying substantially in said detect zone, being spherically curved about said center point, and light scattered by a particle passing through said detect zone passes through said glass-like material and emerges largely normal to said spherically curved outer surface portion before passing to one of said detectors;

said detectors being located outside said carrier, and light scattered from said detect zone to a detector travels through said spherical outer surface portion to reach the detector.

6. The apparatus described in claim 5 wherein:

said fluid has a predetermined index of refraction and said glass-like material has an index of refraction greater than that of said fluid;

said beam path extends in a forward direction;

a plurality of said detectors each lies from said detect zone forward of said passage and detects light scattered at an angle of at least 50° from said beam path.

* * * * *